United States Patent [19]

Folkenroth et al.

[11] 4,344,756
[45] Aug. 17, 1982

[54] WATER RECYCLER FOR DENTAL OPERATORIES

[75] Inventors: Richard P. Folkenroth, Dover; Thomas J. Dunn, Red Lion, both of Pa.

[73] Assignee: Dentsply Research & Development Corp., Milford, Del.

[21] Appl. No.: 305,824

[22] Filed: Sep. 28, 1981

[51] Int. Cl.³ ............................................ A61C 17/04
[52] U.S. Cl. ........................................ 433/92; 4/263
[58] Field of Search .................... 433/27, 92, 95, 97, 433/91; 4/263, 262; 137/624.11

[56] References Cited

U.S. PATENT DOCUMENTS 3,482,312 12/1969 Stram .
3,964,112 6/1976 Plowman .
4,245,989 1/1981 Folkenroth et al. .

*Primary Examiner*—Robert Peshock
*Attorney, Agent, or Firm*—C. Hercus Just

[57] ABSTRACT

A water recycling unit and system for dental operatories for use to supply operating priming water to liquid seal type vacuum pumps and including a conduit connectable to a municipal water supply, a solenoid valve in said conduit operated by a timer to open the valve for very short intervals periodically to furnish fresh makeup water to an air-water separator mounted above the level of the pumps and provided with a discharge to drain that is regulated to maintain a constant supply of contaminated water withdrawn from a patient's mouth and a small amount of the makeup water to comprise priming water delivered to the vacuum pump by gravity flow. The only moving element in the basic system is the solenoid valve and it only passes fresh municipal water free of impurities to insure complete closing of the valve and thereby obviate possible partial opening due to impurities lodged between the valve and its seat.

3 Claims, 2 Drawing Figures a
WATER RECYCLER FOR DENTAL OPERATORIES

BACKGROUND OF THE INVENTION

The present invention pertains to a simplified water recycling system for use in dental operatories in which evacuation of fluid from a patient's mouth which includes impurities, such as saliva, tooth and metal chips, and the like, occur by means of vacuum pumps having liquid seals by which the pumps are primed and a residual amount of liquid is maintained in the pumps at all times for insuring adequate sealing at initial startup. A system comprising the present invention offers substantial simplification over systems currently in use, as well as certain advantages thereover described in detail hereinafter.

Liquid seal vacuum pumps have been employed in dental evacuating systems, particularly since the introduction of discharging flushing water into a patient's mouth while certain chipping and grinding operations are performed by a dentist, and therefore, it has been necessary to develop so-called high volume evacuating systems to constantly withdraw the flushing water, saliva and impurities from the oral cavity of a patient. Typical examples of such systems used heretofore are illustrated in prior U.S. Pat. Nos. 3,482,313 to Stram, dated Dec. 9, 1969, 3,964,112 to Plowman, dated June 22, 1976, and 4,245,989 to Folkenroth et al, dated Jan. 20, 1981. In the system of the Stram patent, fresh water is constantly introduced approximately to the extent of two hundred forty gallons per normal working day, and this water, after passing through the pump, engages a liquid and air separator and the water is discharged entirely to a drain.

In the systems of the Plowman and Folkenroth et al patents attempts to conserve water consumption are disclosed, particularly the water received from the cuspidors of dental operatories, by the Plowman patent filtering the contaminated water and recirculating at least part of it through the liquid seal pumps to maintain the same in primed condition. The Folkenroth et al patent recirculates contaminated water to the pumps to effect the seal thereof and effects certain economies in water consumption. However, these systems are relatively extensive and complex, in contrast to the far more simple system of the present invention which is directed to water conservation, but in which system no contaminated water passes through control valves which conceivably could remain at least partially open in the event contaminated water passed through the same and some of the contamination became lodged between the valve member and seat of the control valve.

SUMMARY OF THE INVENTION

It is among the primary objects of the present invention to provide a water recycling unit and system for use in dental laboratories to supply operating priming water to the liquid seal type vacuum pumps which develop suction to withdraw water from the oral cavity of patients in which saliva and solid impurities usually are entrained, said contaminated liquid, known as "gray water", is recirculated through the pumps continuously to provide continuous priming thereof, the "gray water" being discharged to an air-water separator in which the storage capacity of the separator is adequate at all times to maintain an ample supply of the "gray water", preferably by gravity flow, to the liquid seal pumps and the system includes a fresh water makeup flow of very minimal amount by means of controlling a solenoid inlet valve for infrequent, very short periods to provide fresh makeup water to the volume of "gray water" in the air-water separator to insure an adequate supply of sealing water to the pump by means of a very minimal amount of fresh water consumption.

It is another very important object of the invention to include in the system a primary control valve in the fresh water supply line operated by a timer to effect such short interval type operation to introduce small quantities of fresh water periodically to the air-water separator, the solenoid-operated valve preferably comprising the sole moving member in the control system and this receives only fresh water passing therethrough, whereby there is no possibility of the valve being "stuck" in slightly open position due to particles of solid contaminating material being lodged between the valve member and seat, as is possible in the control systems of the aforementioned patents, due to the fact that the control valves in said systems have "gray water" passing therethrough and it is known that under certain circumstances, valves have been stuck in open position, especially at the end of the day's operation, whereby flooding of operatory floors has occurred, resulting in substantial damage.

Details of the foregoing objects and of the invention, as well as other objects thereof, are set forth in the following specification and illustrated in the accompanying drawings comprising a part thereof.

DETAILED DESCRIPTION OF THE PREFERRED EMBODIMENTS

Figure 1:
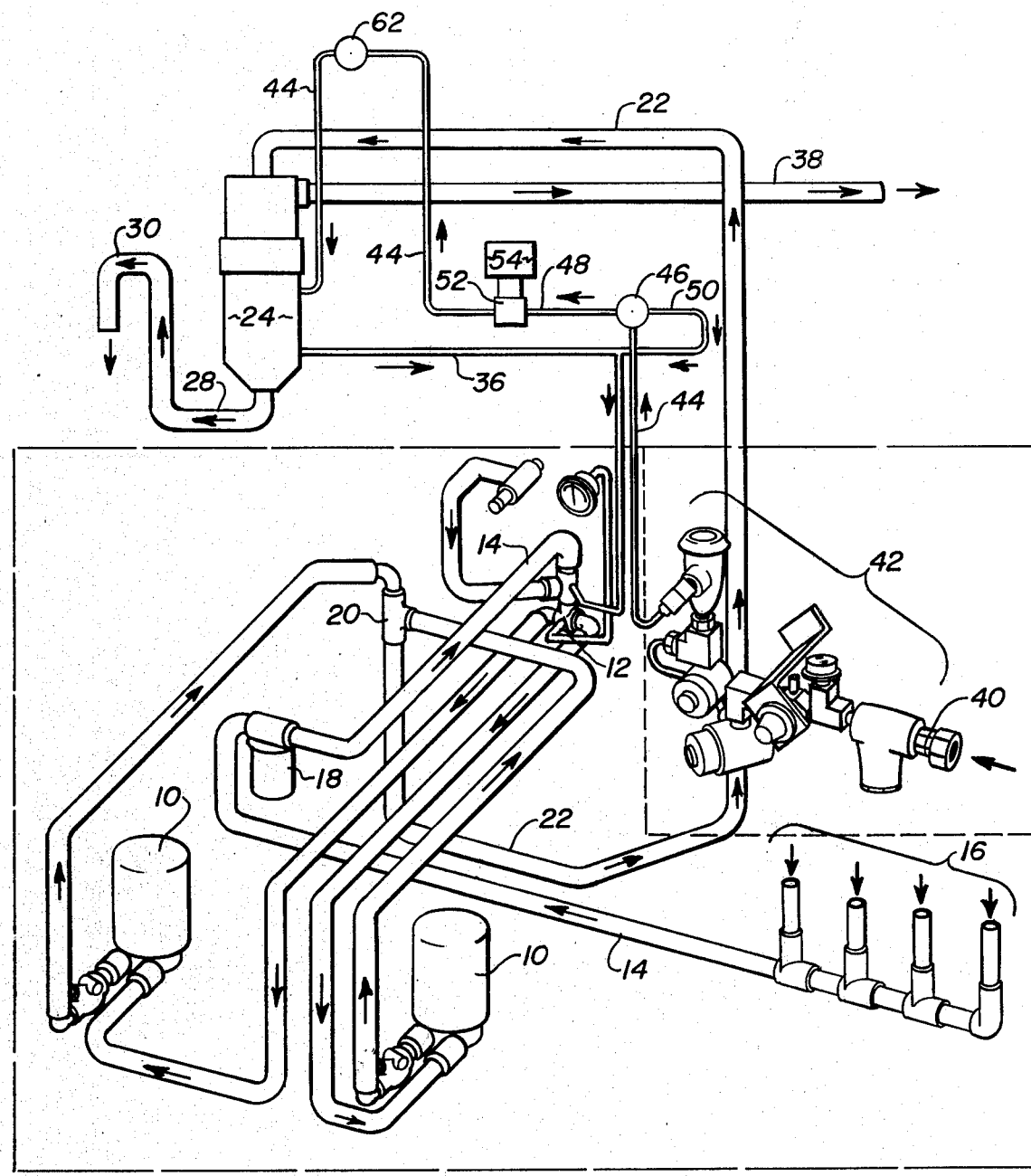
FIG. 1 is a diagrammatic perspective view of a water recycling system embodying a pair of liquid seal suction pumps and including conduits to and from the same, as well as from dental operatories, as illustrated in a rectangular broken frame, and also including in the upper part of the figure, the improvement afforded by the present invention comprising an air-water separator used as the supply reservoir of "gray water" to the liquid seal pumps.
Figure 2:
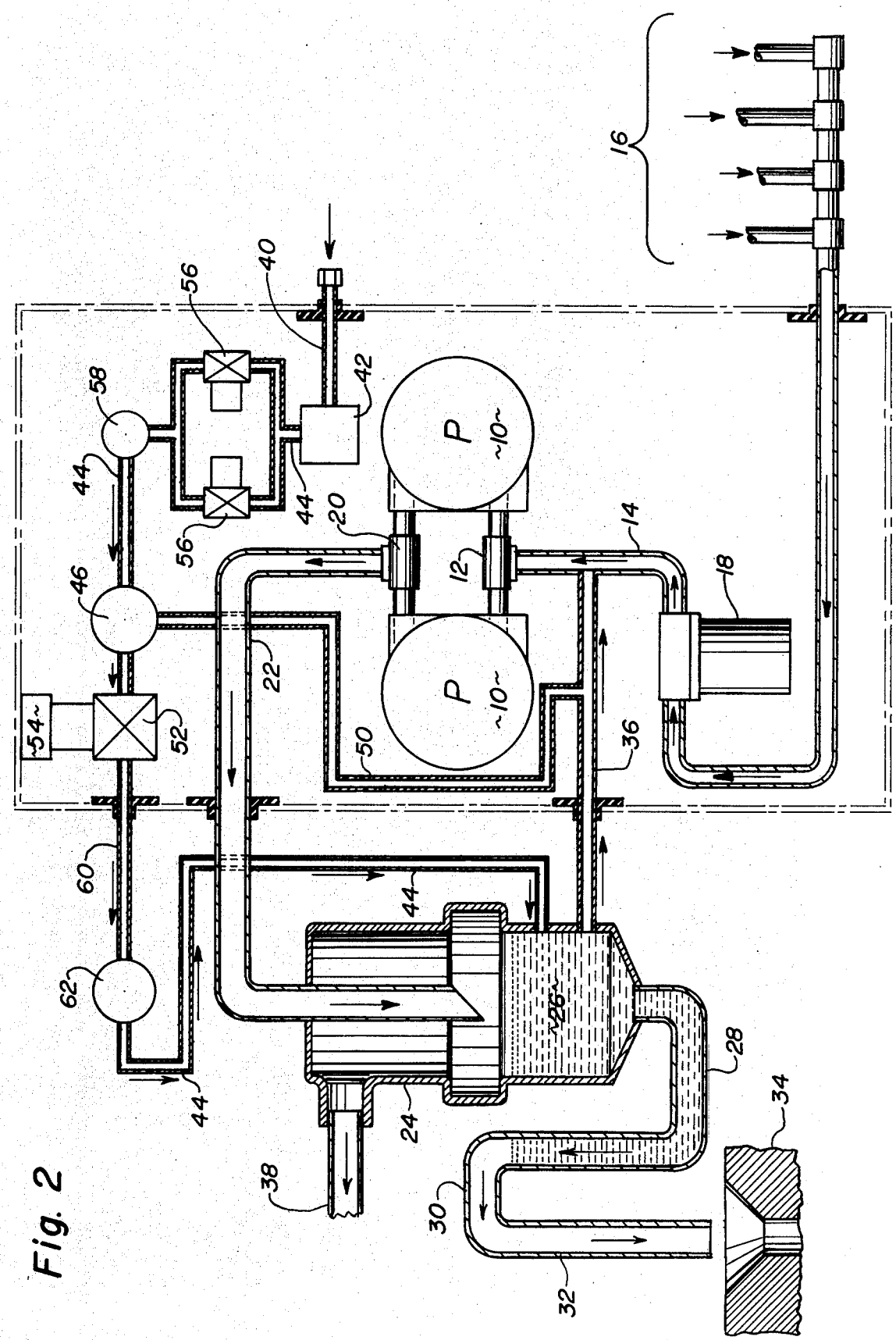
FIG. 2 is a vertical sectional view, showing certain of the key features of the system shown in FIG. 1, but illustrating details of the components of the system in a somewhat graphic manner.

For purposes of orienting the present invention with respect to known devices, particularly by referring to FIG. 1, in which a single broken line rectangle is shown, which corresponds to the double broken line rectangle in FIG. 2, the apparatus illustrated therein is very similar to a double pump, high volume evacuator, such as shown in prior U.S. Pat. No. 3,964,112, in which a single pump is illustrated and, more particularly, prior U.S. Pat. No. 4,245,989 over which the present invention to a large extent constitutes an improvement by simplifying the apparatus shown in said patent. Both of said patents are assigned to the assignee of the instant invention.

The structure shown within the aforementioned broken line rectangles comprises a pair of similar liquid seal vacuum pumps 10, which are similar to pumps 10 and 12 in the 4,245,989 patent. These pumps are connected by a tee 12 to an inlet conduit 14, which receives "gray water" from operatory inlets 16, the conduit 14 including a solids collector 18, similar to the collector 26 in U.S. Pat. No. 4,245,989. An important purpose of the present invention is to always provide sufficient water within the pumps 10 that there is no need to prime the same at startup. Moreover, the system of the present invention provides means by which the so-called "gray water" cannot enter the fresh water supply introduced into the system and thereby risk contaminating the same.

Another tee 20 commonly receives discharge from pumps 10 and conducts the same through conduit 22 to the air-water separator unit 24. The separator unit 24 preferably is mounted vertically and is arranged to maintain a reservoir of "gray water" 26 at a suitable level controlled by the U-shaped discharge conduit 28, the conduit 28 actually constituting a double U-shaped configuration, the second U-shaped portion of the conduit being at a level commensurate with the amount of water desired to be maintained in the reservoir 26, and then having a depending discharge section 32 which discharges into a drain 34. An essential feature of the present invention constitutes the fact that the lower portion of the "gray water" reservoir 26 discharges through conduit 36 by gravity to the inlet conduit 14 and tee 12 into the inlet of the respective pumps 10. By means of the gravity flow, and the maintenance of a satisfactory level in the reservoir 26, there will always be ample sealing water for the pumps 10, in accordance with the present invention. The upper portion of the separator unit 24 has an air discharge conduit 38 extending outwardly to atmosphere.

Because of evaporation and otherwise, it is essential that the desired amount of water be maintained in the "gray water" reservoir 26 for gravity flow to the pumps 10 and to accomplish this, regardless of the amount of water obtained from the operatory inlet 16, and also for the safety purpose of not contaminating fresh water supply with said "gray water", the present invention provides a fresh water inlet conduit 40. The fresh water passes through certain regulating elements, commonly encompassed by a bracket 42, details of which are described in aforementioned U.S. Pat. No. 4,245,989, the fresh water exiting from the regulating elements 42 by a conduit 44 to a three-way valve 46, having two outlets 48 and 50, outlet 48 being connected to a solenoid-operated valve 52, controlled by a timer 54 and the other outlet 50 constituting a bypass to the discharge conduit 36, for purposes to be described.

In FIG. 2, which is somewhat diagrammatic, it will be seen that the conduit 44 includes a pair of solenoid valves 56, which are part of 42 in FIG. 1 and actually constitute valves which are turned on at the beginning of day's operation, for example, and remain on during the entire period of operation, the same being closed at the end of the day, whereby they are somewhat in the nature of master control solenoid valves. The discharge from these valves communicate with a vacuum breaker 58, which is included in conduit 44 prior to the three-way valve 46. Discharge conduit 60 leads from the timer actuated solenoid valve 52, and the fresh water therein passes through another vacuum breaker 62 which also is shown in FIG. 1. In FIG. 1, the outlet 48 from the three-way valve 46 actually is part of the conduit 44, which leads to the vacuum breaker 62 and discharges through another portion of conduit 44 into the lower portion of the separator unit 24 at a level above the discharge conduit 36, which is also connected to the separator unit, as clearly shown in both FIGS. 1 and 2.

The primary purpose of the present invention is to introduce in a very conserving manner, fresh water to the reservoir 26 at spaced intervals of very short duration. By way of example, the intervals may be of the order of forty seconds but the valve remains on only four seconds at each of these intervals, whereby it will be seen that a relatively small amount of water is required to furnish the makeup for the water normally required by the pumps. It also is to be understood that the time example set forth above is essentially illustrative rather than being of a restrictive nature since, depending upon operating conditions, variations in the "on" and "off" periods may be necessary, but the specific illustration is primarily set forth to illustrate the possible economy in consumption of fresh water. This economy is effected by a substantially more simple system than that of prior U.S. Pat. No. 4,245,989, due to the elimination of the tanks 76 and 78 thereof and employing only the air-water separator unit which is used as a reservoir for the "gray water" and thus, it is a distinction over the use of the separator in U.S. Pat. No. 4,245,989.

As an example of water economy over that of the earlier Stram U.S. Pat. No. 3,482,313, conventional operation thereof required a consumption of approximately thirty gallons of water per hour. The average consumption by the recycler of the present invention is of the order of about one-tenth of that of the Stram system, or approximately three gallons per hour. Also, another recommended time period for use of the present invention, based upon a per hour rate is to have the valve open for periods of six seconds each hour, which constitutes a certain amount of saving of operation of the valve in mechanical wear. It also is obvious that the system of the present invention is substantially more simple than that of prior Plowman U.S. Pat. No. 3,964,112, in addition to the fact that the Plowman patent is concerned with recycling cuspidor water, whereas the present invention primarily is concerned with recycling "gray water", resulting from flushing oral cavities of patients to remove cooling and flushing water therefrom.

In the event either the solenoid valve 52 or timer 54 should malfunction in a manner so as not to supply water to the separator unit 24, from which water for sealing the pumps 10 is received, the system normally would lose its prime after a period of time, such as about one hour, and would thereafter no longer supply vacuum to the system. Should such situation occur, the three-way valve 46 can be moved to activate outlet 50, which will cause fresh water to be delivered to conduit 36 and discharge such fresh water into inlet conduit 14, which leads to tee 12 and pumps 10. Such an arrangement will at least permit the operatory system to function until suitable restoration of the normal function of solenoid valve 52 and timer 54 can be resumed, following repair or replacement. It will be understood that the foregoing operation is merely of the nature of an emergency and normally will not result in water economy.

Another attribute and advantage of the present invention as illustrated in FIG. 1 resides in the fact that the solenoid valve which is actuated by timer 54 constitutes the only moving member in the fresh water supply system for the air-water separator unit 24. Especially in the system of prior U.S. Pat. No. 4,245,989, "gray water" circulates through certain of the control valves, and in the event solid waste material becomes lodged between the movable valve member and its seat, closing of the valve is not possible and leakage will occur, sometimes resulting in substantial damage to the floor of a dental operatory or otherwise. In contrast to this, the inclusion of only a single inlet control valve for introducing makeup water to the pumps, it will be seen that only clean water, free of contamination of any kind, especially solid particles or the like, will pass through the control valve and thereby eliminate the possibility of the supply valve remaining open, thus constituting a safety factor.

From the foregoing, it will be seen that the present invention provides a relatively simple system to supply makeup water of a clean fresh nature, free of contamination, to one or more vacuum pumps, the supply being operated by a controlled cycle of minimum periods occurring in cycles of much longer periods of time, but being operable to insure the constant presence of sealing fluid in the air-water separator unit for delivery by gravity to the pumps, thereby insuring the presence of an adequate supply of water, which essentially is "gray water" to provide suitable sealing for the pumps and thereby insure the production of required vacuum to dental operatories, resulting in substantial economy in fresh water consumption automatically controlled by a timer, which actuates the sole movable element in the fresh water supply line to the air-water separator from which the sealing water is derived.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. A dental evacuating system for operatories to withdraw debris and liquids from the oral cavity of dental patients comprising in combination,
   a. water seal-type vacuum pump means requiring a supply of water at all times and including inlet and discharge ports,
   b. conduit means leading from an operatory to the inlet port of said pump means,
   c. an air-water separator unit including a tank having inlet and discharge means, said discharge means being at a level above said inlet ports of said water seal vacuum pump means to provide feed by gravity,
   d. exhaust conduit means leading from the discharge port of said pump means to the inlet means of said separator unit,
   e. at least the lower portion of said tank serving as a water reservoir to supply sealing water to said pump means by gravity,
   f. discharge means on said tank arranged and operable to maintain a minimum amount of water therein at all times,
   g. fresh water conduit means connectable to a supply of municipal water,
   h. a flow-control valve connected to said fresh water conduit means,
   i. a timer connected to said valve and operable to open the same for successive very short predetermined intervals of time to permit limited flow of fresh water therethrough, and
   j. delivery conduit means for said fresh water connected at one end to said valve and at the other end to the lower portion of said tank to deliver fresh water intermittently to said tank as controlled by said valve to maintain said minimum amount of water therein at all times,
   k. whereby only fresh water passes through said flow control valve, thereby obviating any possible clogging of said valve with debris as where "gray water" passes through the valve, and said short intervals of timed delivery of fresh water to said tank affords economy in water consumption.

2. The evacuating system according to claim 1 further including a three-way valve in said fresh water conduit means having one inlet port and two discharge ports respectively directing flow to said inlet means of said air-water separator and a bypass conduit to said conduit means leading to the inlet port of said pump means.

3. The evacuating system according to claim 1 in which said discharge means on said tank operable to maintain a minimum amount of water therein comprises a U-shaped water trap having one leg connected to the discharge means of said air-water separator and the other leg extending upward at least to a level desired to be maintained in said tank and then reversely extending downward for discharge to a drain.

* * * * *